United States Patent
Zubiate

(10) Patent No.: US 11,638,616 B2
(45) Date of Patent: May 2, 2023

(54) SYSTEM AND METHOD FOR CONTROLLING A ROBOT ARM

(71) Applicant: DEPUY IRELAND UNLIMITED COMPANY, Cork (IE)

(72) Inventor: Brett Zubiate, Duxbury, MA (US)

(73) Assignee: DEPUY IRELAND UNLIMITED COMPANY, Cork (IE)

( * ) Notice: Subject to any disclaimer, the term of this patent is extended or adjusted under 35 U.S.C. 154(b) by 392 days.

(21) Appl. No.: 16/574,321

(22) Filed: Sep. 18, 2019

(65) Prior Publication Data
US 2021/0077204 A1 Mar. 18, 2021

(51) Int. Cl.
| | |
|---|---|
| *A61B 34/30* | (2016.01) |
| *B25J 9/16* | (2006.01) |
| *B25J 13/08* | (2006.01) |
| *A61B 90/00* | (2016.01) |
| *A61B 17/14* | (2006.01) |

(52) U.S. Cl.
CPC ............. *A61B 34/30* (2016.02); *A61B 17/14* (2013.01); *A61B 90/06* (2016.02); *B25J 9/1633* (2013.01); *B25J 9/1694* (2013.01); *B25J 13/08* (2013.01); *A61B 2090/064* (2016.02)

(58) Field of Classification Search
CPC ......... A61B 34/30; A61B 17/14; A61B 90/06; A61B 2090/064; A61B 34/75; B25J 9/1633; B25J 9/1694; B25J 13/08; B25J 9/1674; G05B 2219/40601; G05B 2219/45117; G05B 2219/45171; G05B 2219/50197
See application file for complete search history.

(56) References Cited

U.S. PATENT DOCUMENTS

| | | | | |
|---|---|---|---|---|
| 2011/0295248 | A1* | 12/2011 | Wallace | ................ B25J 9/1689 606/33 |
| 2012/0248167 | A1* | 10/2012 | Flanagan | ............... A61B 34/30 227/2 |
| 2015/0342689 | A1 | 12/2015 | Kamon et al. | |
| 2016/0207197 | A1* | 7/2016 | Takahashi | ............. B25J 9/1676 |
| 2016/0361125 | A1* | 12/2016 | Balicki | .................... B25J 19/06 |
| 2017/0080558 | A1* | 3/2017 | Cann | ..................... B60L 3/0061 |
| 2017/0296180 | A1* | 10/2017 | Harris | .................... G16H 20/40 |
| 2018/0157238 | A1 | 6/2018 | Gogarty et al. | |
| 2019/0099886 | A1* | 4/2019 | Chattopadhyay | ...... B25J 9/1674 |

(Continued)

OTHER PUBLICATIONS

International Search Report and Written Opinion of the International Searching Authority re PCT/EP2020/074368 filed Sep. 1, 2020; dated Dec. 12 2020; 13 pgs.

*Primary Examiner* — Abby Y Lin
*Assistant Examiner* — Dylan M Katz
(74) *Attorney, Agent, or Firm* — Kramer & Amado, P.C.

(57) ABSTRACT

A control method is provided to manage a surgical robot having an arm configured to hold a medical tool. The method includes receiving a set of sensor signals from sensors on the arm, generating a profile based on the set of sensor signals, comparing the profile to at least one signature, determining a state of the arm based on results of the comparison, and changing operation of the arm based on the state of the arm. The state of the arm is indicative of a predetermined condition that has occurred or will likely occur eminently. Changing operation of the arm prevents the condition from occurring or continuing. The robot arm may hold a medical tool for using during surgery or another medical procedure.

20 Claims, 9 Drawing Sheets

(56) References Cited

U.S. PATENT DOCUMENTS

2019/0107454 A1    4/2019  Lin et al.
2020/0023525 A1*  1/2020  Miyamoto ............. B25J 19/063
2021/0052340 A1*  2/2021  Rabindran ......... A61B 17/2909

* cited by examiner

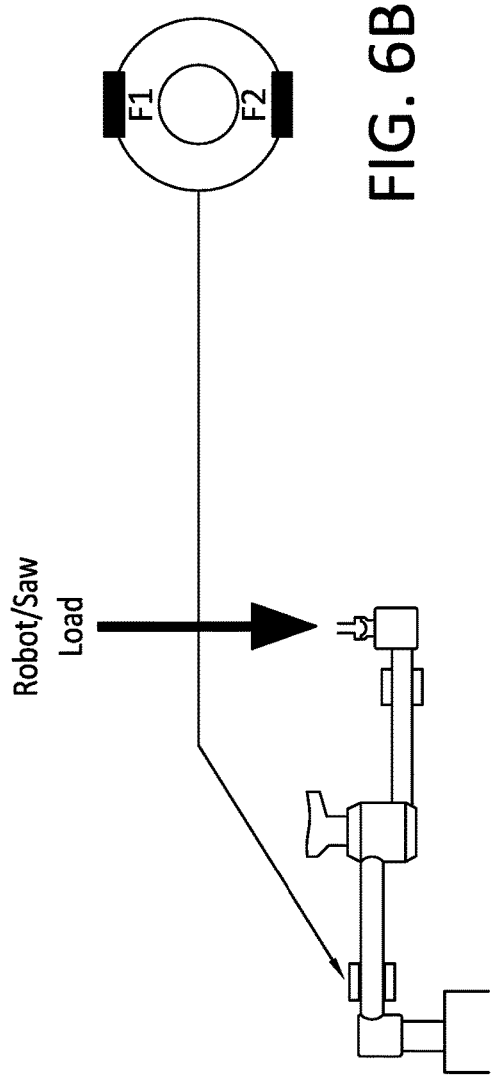
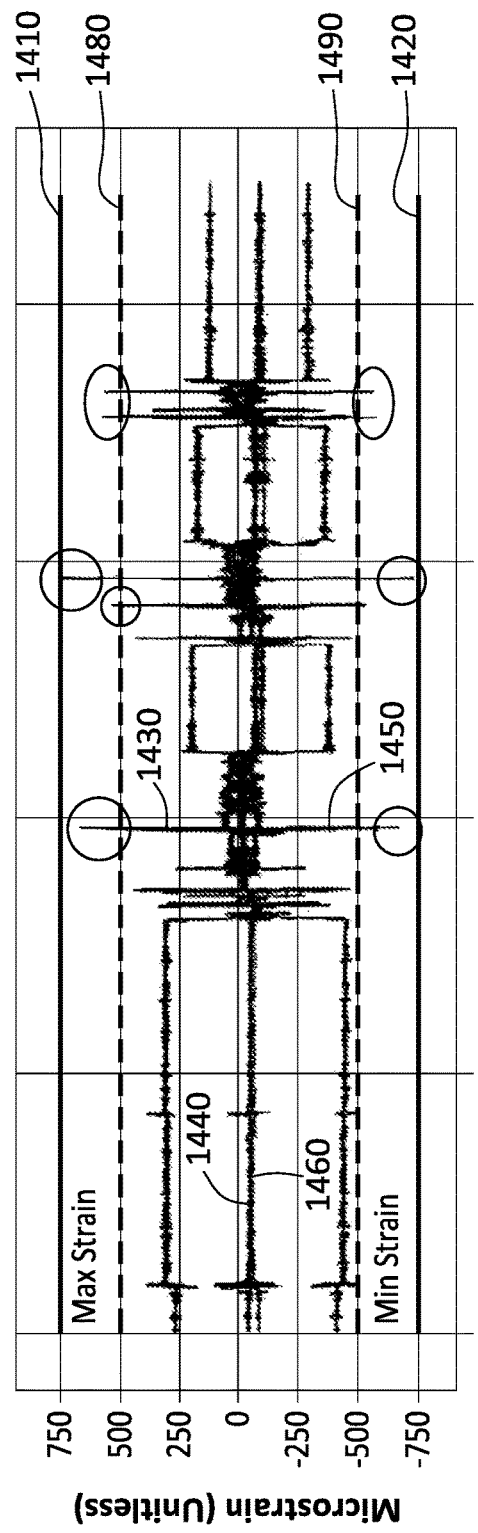

SYSTEM AND METHOD FOR CONTROLLING A ROBOT ARM

TECHNICAL FIELD

Example embodiments disclosed herein relate generally to controlling a robot, and more specifically to a system and method for controlling a robot arm to perform a procedure.

BACKGROUND

Robot arms have been developed to manufacture cars, fabricate integrated circuit chips, retrieve hazardous materials, and perform robotic medical procedures. In this latter case, it is believed that robotic surgery will prove to be more accurate and able to access many areas of the body that are not easily accessible by human surgeons. As a result, many institutions have turned their attentions towards developing surgical robotic arms.

However, surgical robotic arms developed thus far have many significant drawbacks which make them a safety risk to patients and therefore practically unusable. For example, while increased accuracy is a primary goal of robotic surgery, robotic arms that presently exist are inaccurate due to malfunctioning sensors, errors in control software, vibrations and other inconsistencies that adversely affect stability, positioning, and precision of movement. These inconsistencies can produce disastrous consequences, especially when robotic arms are used to perform amputations, brain surgery, and/or other operations that require an acute level of precision.

SUMMARY

In accordance with one or more embodiments, a method for managing a robot includes receiving a set of sensor signals from sensors on an arm, generating a profile based on the set of sensor signals, comparing the profile to at least one signature, determining a state of the arm based on results of the comparison, and changing operation of the robot arm based on the state of the arm, wherein the state of the arm is indicative of a predetermined condition that has occurred or will likely occur eminently and wherein changing operation of the arm prevents the condition from occurring or continuing. The set of sensor signals may include one or more sensor signals, and the set of sensor signals may be generated by strain gauges or other types of sensors as described herein.

The set of sensor signals may include one or more strain signals. The set of sensor signals may include one or more accelerometer signals, gyro signals, potentiometer signals, or Linear Variable Differential Transformer and Transducer (LVDT) signals. The at least one signature may include a vibration profile. Changing operation of the arm may be performed when the profile matches the at least one signature by a predetermined percentage. The at least one signature may include at least one margin value, the state of the arm may correspond to at least one of the set of sensor signals having a value in a predetermined range that is less than a sensor value corresponding to condition, and the margin value may correspond to a lower value of the predetermined range.

The at least one signature may include a value of a first strain signal at a first time, comparing the profile to the at least one signature includes comparing a value of the first strain signal at a second time to the value of the first strain signal at the first time, and determining the state of the arm includes determining that a difference between the value of the first strain signal at the first time and the value of the first strain signal at the second time is greater than a predetermined difference value.

Changing operation of the arm may include disabling operation of the arm for at least a temporary period of time. The condition may correspond to a force on the arm that causes the arm to deviate in an unintended direction. The condition may correspond to a force on the arm caused by a bump or vibration. The condition may correspond to improper or unsafe locking state of the robot arm during an operation.

In accordance with one or more other embodiments, a system for managing a surgical robot having an arm configured to hold a medical tool includes an interface configured to receive a set of sensor signals; a memory configured to store one or more algorithms; and processor configured to execute the one or more algorithms to control the arm that includes sensors that generate the set of sensor signals, the one or more algorithms to generate a profile from the set of sensor signals, compare the profile to at least one signature, determine a state of the arm based on results of the comparison, and generate signals to change operation of the arm based on the state of the robot arm, wherein the state of the arm is indicative of a predetermined condition that has occurred or will likely occur eminently and wherein changing operation of the arm prevents the condition from occurring or continuing.

The set of sensor signals may include a set of strain signals. The set of sensor signals may include one or more accelerometer signals, gyro signals, potentiometer signals, or Linear Variable Differential Transformer and Transducer (LVDT) signals. The at least one signature may includes a vibration profile. Changing operation of the arm may be performed when the profile matches the at least one signature by a predetermined percentage.

The at least one signature may correspond to at least one margin value, the state of the arm may correspond to at least one of the set of sensor signals having a value in a predetermined range that is less than a sensor value corresponding to the condition; and the margin value may correspond to a lower value of the predetermined range. The at least one signature may include a value of a first strain signal at a first time; and the one or more algorithms may cause the processor to compare a value of the first strain signal at a second time to the value of the first strain signal at the first time and determine that a difference between the value of the first strain signal at the first time and the value of the first strain signal at the second time is greater than a predetermined difference value. The one or more algorithms may cause the processor to disable operation of the robot arm for at least a temporary period of time. The condition may correspond to a force on the arm that causes the arm to deviate in an unintended direction.

BRIEF DESCRIPTION OF THE DRAWINGS

Additional objects and features of the invention will be more readily apparent from the following detailed description and appended claims when taken in conjunction with the drawings. Although several example embodiments are described, like reference numerals identify like parts in each of the figures, in which:

FIGS. 6A to 6C illustrate detection of a state of a robot arm according to one embodiment;

DETAILED DESCRIPTION

The descriptions and drawings illustrate the principles of various example embodiments. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various example embodiments described herein are not necessarily mutually exclusive, as some example embodiments can be combined with one or more other example embodiments to form new example embodiments. Descriptors such as "first," "second," "third," etc., are not meant to limit the order of elements discussed, are used to distinguish one element from the next, and are generally interchangeable. Values such as maximum or minimum may be predetermined and set to different values based on the application.

Figure 1:
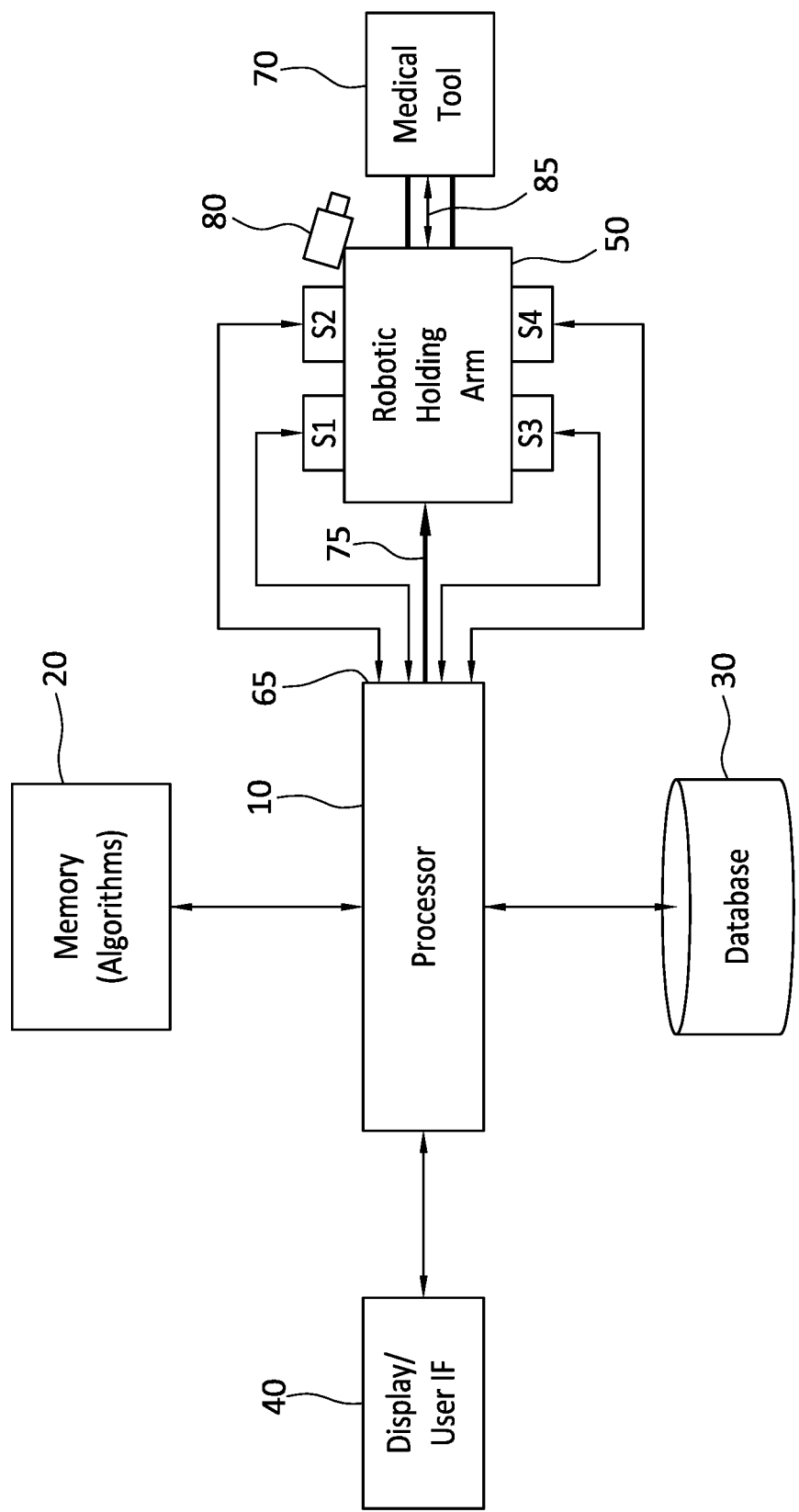
FIG. 1 illustrates an embodiment of a system for controlling a robot arm.

FIG. 1 illustrates a system for controlling the holding arm of a tool used to perform various medical procedures. This is accomplished by processing information to determine patterns that may lead to an anomaly affecting the operation and stability of the holding arm. By recognizing these patterns, the system is able to take preemptive action to avoid the anomaly before it occurs, thereby securing patient safety and the potential success of the operation. The medical tool held and guided by the arm may be a drill, scalpel, saw, probe, sensor, cauterizing electrode, catheter, syringe, endoscopy, or another type of tool for performing a patient procedure.

Referring to FIG. 1, the system includes a processor 10, a memory 20, a database 30, and a display 40, which, for example, may also operate as a user interface (IF). The processor 10 executes one or more control algorithms stored in the memory 20 in order to recognize patterns that may lead to an anomaly relative to a robotic holding arm 50, as described above. The processor performs these functions, at least in part, based on information received from one or more sensors mounted on or proximate to the robotic holding arm. The information may be received, for example, through an interface 65.

In the example of FIG. 1, four sensors S1 to S4 are shown but a different number of sensors may be included in another embodiment. The processor 10 may generate control signals for selected ones of the sensors, for example, in order to activate them and/or to change their mode of operation. The processor 10 may also receive images from at least one camera 80 mounted on or near the robotic holding arm and/or a medical tool 70 held and controlled by the arm. For illustrative purposes, the medical tool will be described as a bone saw that is used to perform total knee arthroplasty procedures.

Based on the patterns that are determined to exist based on the information collected from the sensors and/or camera, the processor 10 may generate one or more control signals 75 for controlling operation of the robotic holding arm 50. In one embodiment, some of these control signals 85 may be output to medical tool 70. Using these signals, the processor 10 may take preemptive action to avoid a malfunction or other anomaly that has at least a predetermined probability of occurring considering the patterns determined to exist. The database 30 may store statistical and/or other data that may be compared to the sensor signals for purposes of determining these patterns. As will be explained in greater detail below, in one embodiment the patterns may include signatures from strain gauges, accelerometers, potentiometers in the joints, gyros, optical tracking sensors, Linear Variable Differential Transformer and Transducer (LVDTs), load cells, torque sensors, pressure sensors, and/or other types of sensors that may be used as a basis for predicting an anomalous condition.

The system for controlling the holding arm may be configured in a variety of ways.

Figure 2:
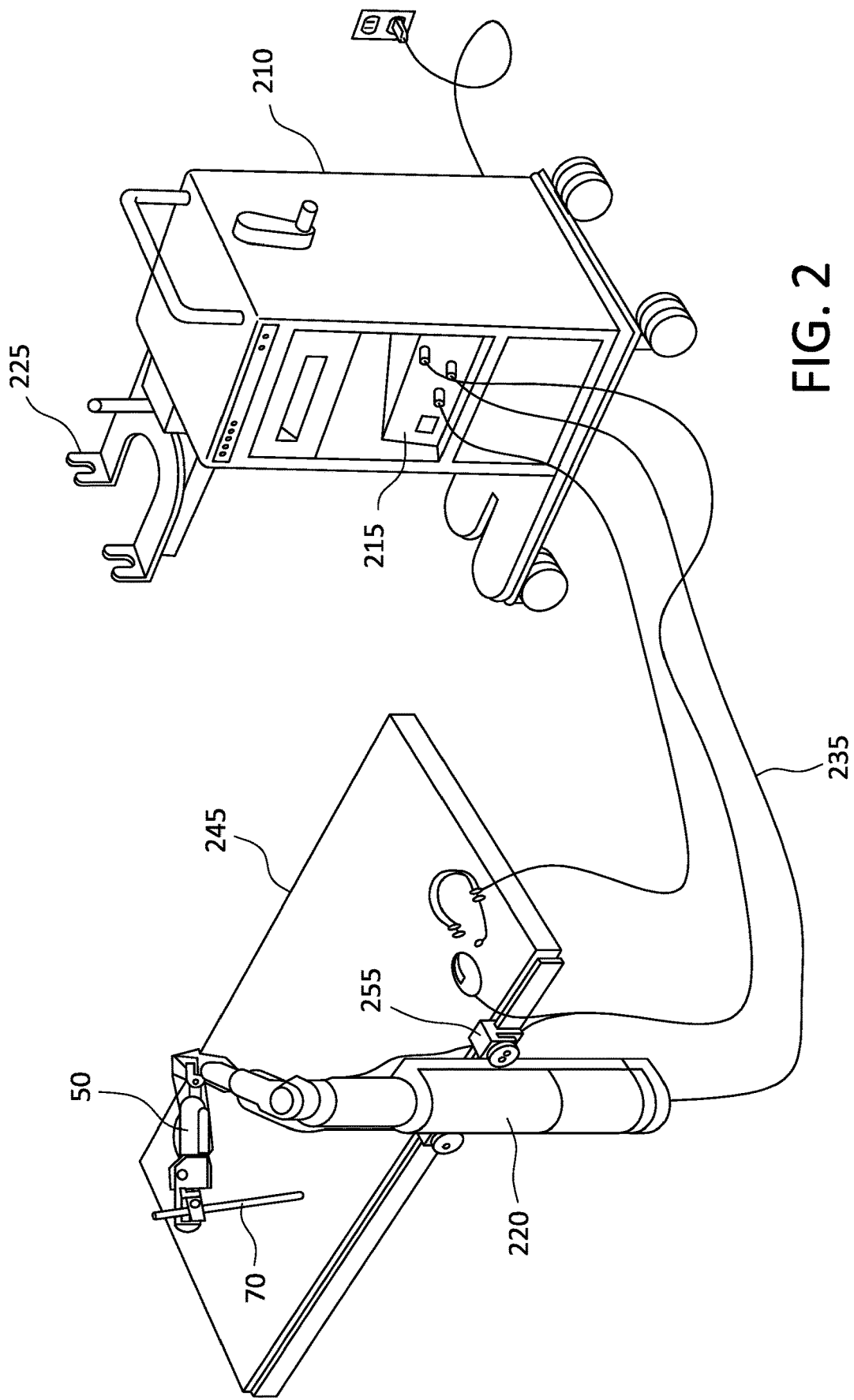
FIG. 2 illustrates an embodiment for attaching a robot including the robot arm.

FIG. 2 illustrates an example of how the system may be configured. Referring to FIG. 2, the system includes a robot 220 that is held within and transported on a cart 210. The cart 210 may be located at a hospital, clinic, doctor office, outpatient or urgent care center, or another medical facility. In a practical application, the cart may be wheeled to a patient location when an operation is to be performed. The robot 220 may be equipped with servo motors and/or other mechanical drives and supports for controlling the robotic holding arm 50 that supports and controls movement of a bone saw or other type of medical tool 70. The cart 210 may also be equipped with equipment 215 for controlling operation of the robot arm and/or processing signals received from the robot arm. In one embodiment, the robot 220 may include the processor 10, the memory 20, and/or the database 30 for executing the algorithms described herein.

The robot 220 may be carried by the cart on a support 225 until the cart arrives at the patient location. At that point, the robot 220 may be mechanically removed from the cart, but may maintain communication with equipment 215 through one or more wires 235. The patient location may be a patient bed, a surgical table in an operating room, or another patient location. For purposes of illustration, the patient location may be described as an operating room including a surgical table 245. When released, robot 220 may be placed at a location proximate the surgical table for operating on the patient. In one embodiment, the robot 220 may be attached to an edge of the surgical table by a clamp or other fastener 255.

Robot Holding Arm Control

Figure 3:
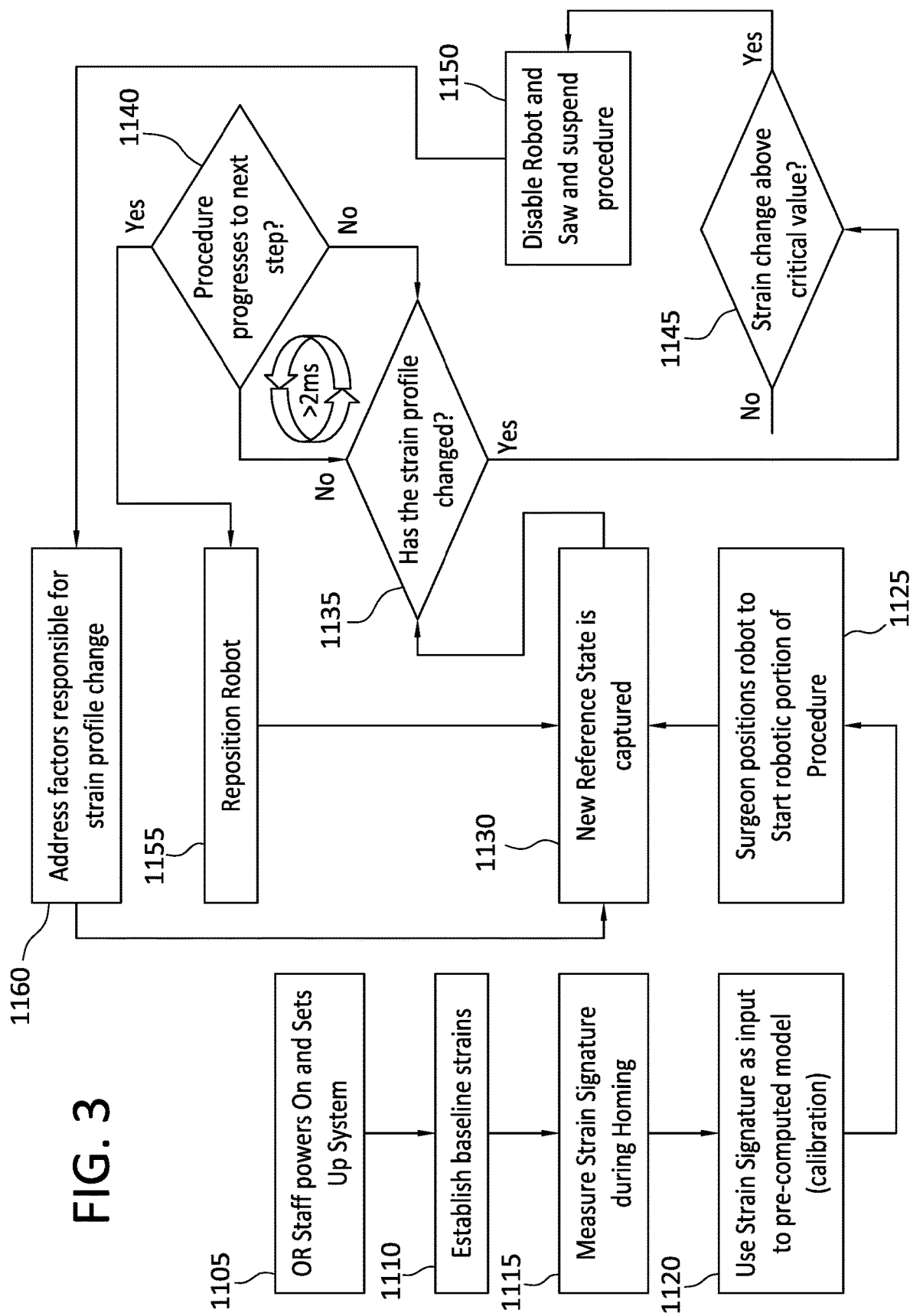
FIG. 3 illustrates an embodiment of a method for controlling a robot arm.

FIG. 3 illustrates an embodiment of a method for controlling the movement and operation of the robot holding arm 50 for purposes of performing an operation using the bone saw 70. The method may be implemented, at least in part, based on one or more control algorithms stored in system memory 20, which, for example, may be included in the robot 220 along with the processor 10 for executing these algorithms. In one embodiment, the control algorithms may be responsive to inputs received by the graphical user interface of the display. The inputs may be entered by a technician, surgeon/doctor, or both, for purposes of setting up the robot and/or moving and controlling the arm and bone saw for performing an operation on a patient. The display may include a touch screen for purposes of receiving the inputs. In addition to control screens for operating the robot arm, the display 40 may output other types of information including patient vital signs.

In one embodiment, the control program(s) for controlling the robot arm match the specific structure of and arrangement of sensors on the robot arm. For example, the robot arm may include one or more segments and/or pivot points that are controlled to allow movement along three axes, in order to allow the medical tool (e.g., bone saw) to be properly positioned relative to body part of the patient being operated on. In one embodiment (e.g., FIG. 4), the robot arm 50 has two segments 51 and 52 and four pivot points 53, 54, and 55 for extending and rotating the bone saw 70 in various directions. The robot arm 50 may have a different number of segments and/or pivot points in another embodiment.

The arrangement of sensors (e.g., S1 to S4 in FIG. 1) on the robot arm may be different, for example, depending upon the structure of the robot arm. The sensors may include strain gauges that detect the strain at predetermined points along the arm. The strain values detected at these points may be processed by an algorithm to generate a strain signature that may be used as a basis for determining the probability of an anomaly prior to the anomaly occurring or as the anomaly is occurring. Action may then be automatically taken based on the algorithm to preempt such an anomaly, thereby protecting the patient and ensuring success of the operation.

Figure 4:
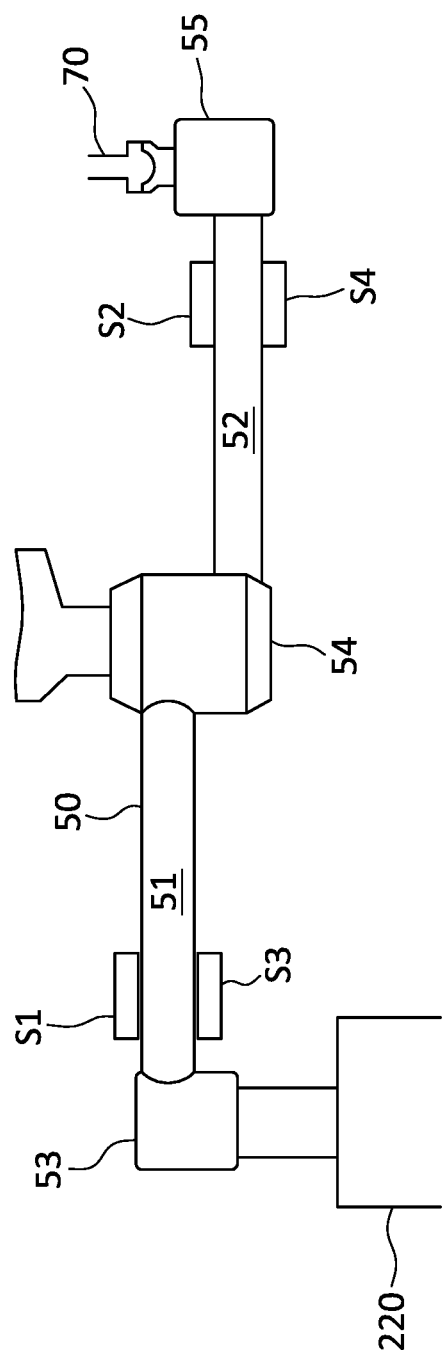
FIG. 4 illustrates an example of an arrangement of robot arm sensors.

FIG. 4 illustrates an embodiment of how sensors S1 to S4 may be arranged relative to the robot arm 50. In this embodiment, the sensors may be strain gauges. Two of the strain gauges S1 and S3 may be arranged on opposing sides of segment 51 of the robot arm and the other two strain gauges S2 and S4 may be arranged on opposing sides of segment 52 of the robot arm. At these locations, the strain gauges (and/or other types of sensors, as previously indicated) are able to detect the loads, vibrations and/or other forces that may bearing upon the position, movement, and operation of the medical tool 70. The types, numbers, and arrangement of sensors in FIG. 4 are only provided as an example. In other embodiments, different type(s), numbers, and/or arrangements of sensors may be used to determine the forces and loads on the robot arm.

Referring to FIG. 3, the method includes, at 1105, powering on and setting up the system. This may involve operating room staff transporting the robot (e.g., by hand, on cart 210, or otherwise) to the location of the patient where the operation is to be performed. Depending on the type of operation to be performed and the medical tool 70 to be used, the patient location may be an operating room including a surgical table, a patient bed, or another location.

At 1110, a set of baseline strain values are established for the robot arm. The baseline strain values may be taken, for example, at a time the robot arm is at rest in order to define a noise floor and an initial offset of strain readings with the system in its initial configuration.

At 1115, a homing procedure is performed which may involve calibrating the robot arm. During the homing procedure, the robot arm may be moved along each of three axes, with the movement along each axis taking place through a predetermined (e.g., entire) range of motion in order to establish respective end stop positions. Measuring strain through this activity may generate signals that may be used to determine initial positions of the robot arm joints (e.g., pivot points).

At 1120, the strain gauge signals generated during the homing procedure are used to generate a strain signature for the robot arm. The strain signature may be generated in various ways. For example, a strain signatures may be generated using a transfer function which maps loading of the holding arm to a specific configuration of the horizontal linkage, as shown in FIG. 4. The specific configuration may include, for example, one or more joint angles of the 3 revolute joints depicted in this figure. The transfer function may be estimated analytically or empirically. Additionally, the specific aggregate static loading of system elements may be interrogated using strain gauges. The combination of sensor values at any given time may represent a strain profile indicating how the robot is positioned at that instant, assuming static or quasi-static conditions. In one embodiment, the strain signature may be a predefined time variation in the strain profile observed with reasonable resolution.

Examples of the types of strain signatures that may be generated include point signatures, profile signatures, and template signatures. Point signatures may describe an aspect or state of specific components or elements of the system. Point signatures may be computed analytically or measured empirically, and may only take into consideration single time points. For example, if a sensor x reads greater than a predetermined value y, then the component(s) to which sensor x is attached is/are approaching yield.

Profile signatures may describe the static pose of the holding arm and robot. In this case, the profile signature may be computed analytically or empirically based on a collection of points. In one embodiment, a profile signature may be computered using a plurality of signals at a single time point. For example, if the sensors read values W, X, Y, Z in static or quasi-static conditions, then the horizontal linkage may be determined to have a configuration C.

Template Signatures may describe system level and subsystem level state changes that potentially can result in hazardous situations. This type of signature may be measured empirically and may be based on a template that includes a collection of profiles. This information in these profiles may be based on any number of sensor signals and, in some cases, even no sensor signals, which would provide information about the system (e.g., a malfunction of some kind). The number of time samples in the measured time series may be at least $T/(1/f)$, where T is the length of time over which the template is generated and f is the sampling frequency of the processor. Thus, for example if the shape of a curve matches the shape of a measured time series, then the template signature would indicate a high likelihood that the measured event matches the known event established empirically by the template.

The strain signature may be used to initialize one or more pre-computed models for the robot. For example, the strain signature may be used to calibrate the pre-computed model(s) for purposes of determining loading conditions of the arm during operation. Once calibrated, the pre-computed model(s) may be used as a basis for predicting anomalies or other types of events when the operation is performed on the patient. The prediction may involve comparing episodic strain signals captured by the sensors to the model(s), as described in greater detail below.

At 1125, the robot 220 is positioned relative to the patient, for example, by attaching the robot to the surgical table or patient bed, for example, according to any of the embodiments described herein. This may be performed, for example, using any of the clamping configurations previously described and adjusting the height and position of the robot to allow the medical tool 70 to be properly positioned relative to the body part of the patient to be operated on. When the robot 220 is transported in cart 210, operation 1125 may also include separating the robot 220 from the cart 210. In one embodiment, the workflow operations to be followed in positioning the robot 220 may be controlled by software. To guide the technician or surgeon in performing these operations correctly, text and/or graphics corresponding to the operations may be output on the display 40.

Once the robot is in position and attached to the surgical table or bed, a registration procedure may be performed based on the type of operation to be performed on the patient. When the operation involves using a bone saw to amputate the foot of the patient, the registration procedure may include acquisition and imageless registration of bony landmarks with tracking arrays used by a vision system to locate the femur, tibia, robot, and bone saw in a global coordinate system.

In one embodiment, the vision system may include one or more motion capture sensors strategically placed on the body of the patient in an area including and proximate to the amputation site, e.g., lower leg, angle, and foot. The motion capture sensors may include, for example, any combination of photosensors, angle sensors, infrared sensors, and optical sensors. A number of additional sensors (e.g., accelerometers, inertial sensors, magnetic bearing sensors, etc.) may also be placed on the body of the patient. Once the sensors are in place, one or more cameras may capture position and orientation data corresponding to the site of the amputation.

Figure 5:
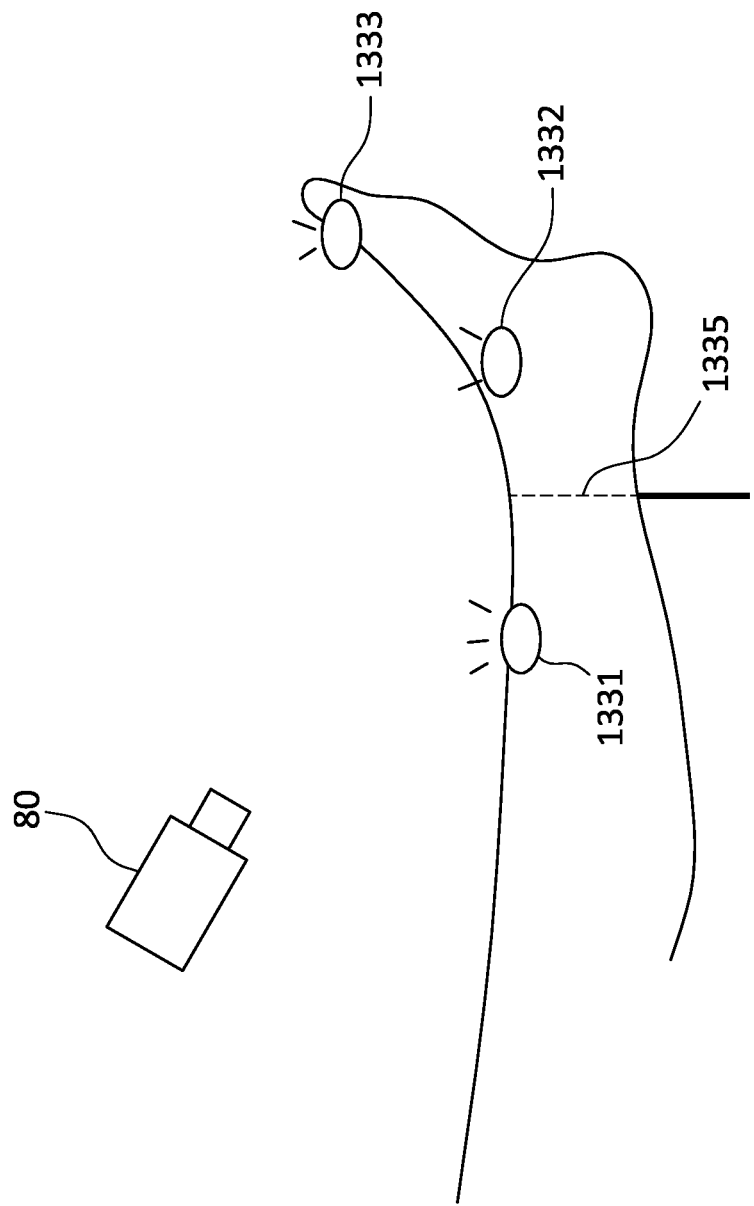
FIG. 5 illustrates an example of sensors arranged on a body part.

FIG. 5 illustrates an example of one of these cameras in the form of camera 80, which is also depicted in FIG. 1. The field of vision of camera 80 includes light emitted or reflected from fiducial markers 1331, 1332, and 1333 arranged in and around the global change amputation to total knee arthroplasty site, marked by dotted line 1335. Additional cameras may be added, for example, at different angles or fields of view to provide additional data. Once the registration procedure and surgical planning has been completed, the surgeon may begin using the bone saw to perform the amputation. In some cases, this may require repositioning the robot to establish the first cutting plane.

At 1130, the method may include capturing a new reference state by the system to establish a new baseline from which to compare future measurements. This operation may be performed, for example, at the inception of the surgery and also whenever there is a repositioning of the robot arm. Repositioning of the arm may cause the arm to experience different loading conditions as determined by the arrangement of sensors (e.g., strain gauges). The new baseline may be performed in a manner similar to establishing the initial baseline, as previously described. Operation 1130 may be considered to be optional in some embodiments. In one embodiment, a plurality of reference states may be determined, where each reference state correspond to a different phase of the operation to be performed by the robot arm and tool and/or a different condition that may exist during the operation.

At 1135, the processor 10 monitors the signals from the sensors S1 to S4, in tandem with the images from the camera(s), to continuously (or incrementally) generate real-time strain signatures (or profiles) for the robot arm. The processor 10 may evaluate the strain profiles generated by the sensors based on an algorithm stored in the memory 20 on or external to the robot. As the strain profiles are generated, the processor 10 may compare the profiles to the reference state determined in operation 1130. As previously indicated, in one embodiment a plurality of reference states may apply. In this case, processor 10 may compare the profiles to one of the reference states that corresponds, for example, to the phase or condition of the operation then taking place. If the processor 10 determines that the strain profile has not changed in a significant way based on the comparison, then the method proceeds to the next operation 1140. In one embodiment, the reference state may be different. In one embodiment, the reference state may include at least one reference value (or set of values) defining a point where a malfunction or other condition may occur with a high probability or is occurring eminently. In one embodiment, the reference state may include at least one range defined by a predetermined maximum value and a predetermined margin value relative to the maximum value. When falling in this range, the processor 10 may determine that a malfunction or other condition may occur with a high probability or is occurring.

In one embodiment, the processor 10 may compare one or more signals from sensors S1 to S4 to one or more prior strain values or profiles. For example, one or more strain signals from sensors S1 to S4 may be compared to immediately preceding strain values or profiles from those sensors or one or more preceding values or profiles generated at another prior time. If the difference between current and prior strain value(s) or profile(s) exceeds a predetermined difference value, then the difference may be determined to be sufficiently significant as to warrant a conclusion that a malfunction or other condition of the robot arm and/or tool may occur with high probability or is occurring during the operation.

In one embodiment, one or more predictive qualities may be obtained as well by taking time into account. An applicable threshold to be used may be based on reaching a specific value, or the decision to change state may be based on the fact that the observed strain values are trending such that they will exceed the threshold in the next predefined window of time (e.g., <10 ms). Thus, if a sensor value has not yet reached the threshold value, but the slope of the curve is steep enough that the next one or two data points will exceed the threshold, the system could stop before the threshold is actually reached.

At 1140, a determination is made as to whether the method should reposition the robot, e.g., position the robot for a next step in the procedure This may be warranted, for example, when a current procedure in the course of the amputation has been completed and the robot arm is to be moved to position the bone saw at another position to enter a next stage of the operation. In another case, the procedure may correspond to a total knee arthroplasty (TKA). In many types of robotic surgery, the robotic arm may not be discretely positioned for specific cuts, but instead is moved in a less structured format. Thus, repositioning in accordance with one embodiment may be performed.

A pre-condition to repositioning the robot arm may be to determine that no inappropriate loading conditions have been detected to exist at that time. If robot arm is not to be repositioned, then the method returns to operation 1135 where the next generated strain profile is compared to the prior strain profile. This method may loop within a predetermined time (e.g., less than 2 ms) until the comparison in operation 1135 determines that the strain profile has changed in a significant way or a determination is made that the robot is to be repositioned in operation 1140.

If, based on the comparison in operation 1135, the processor 10 determines that the strain profile has changed in a significant way or is trending in such a way that the change has been determined to be eminently be significant, then the method will perform a second check. An alarm may or may not be triggered at this time. The change in the strain profile may be considered to be significant, for example, when the difference between the current strain profile and the reference state and/or one or more prior strain values or profiles is greater than a predetermined amount. The type of alarm that is triggered may be determined, for example, based on the type of change between the current profile and the reference state/prior values or profile(s).

At 1145, the change in the strain profile is compared to a predetermined critical value. If the change is equal to or below the critical value, then the method returns to operation 1135 to continue to monitor changes in the strain profile. If the change is above the critical value, then the processor 10 may determine that an anomalous condition is likely to occur in the very near future. This may involve, for example, the processor 10 analyzing data trends over time and also triggering when the data is trending such that it will exceed the threshold, for example, in <10 ms.

In one embodiment, this operation may involve signature matching. In this case, the embodiments described herein relating to comparison to a threshold may be performed in the same manner except comparison to a threshold is replaced with or includes comparison to a signature. Signature matching may then involve determining a percentage or score indicating how well a profile matches the signature.

At 1150, in order to prevent the anomaly from occurring, the processor may generate a signal to disable the robot arm 50 and bone saw 70 and suspend operation. If the robot and bone saw are not active at this time, the processor 10 may prevent the robot and saw from being placed into an active state. Taking these preemptive measures before the anomaly occurs (or as it is just occurring) protects the safety of the patient from injury, which may be acute in the case where the medical tool is a bone saw.

The critical value or condition may be based on the type of anomaly (or other event) that is detected to likely occur or exist. The critical value may be, for instance, an instantons peak load or a matching score generated by a cross-correlation algorithm that involves comparing a transient dynamic strain gauge response to a specific type of event. The anomalies may include, but are not limited to, excessive vibration, inadvertent bumps to the robot arm or surgical table/bed and earthquakes, to name a few. An example of a cross-correlation algorithm is one that analyzes time series data and compares different signals for alignment. In one embodiment, the cross-correlation algorithm may be performed based on the following equation:

$$r = \frac{\sum_i [(x(i) - mx) * (y(i - d) - my)]}{\sqrt{\sum_i (x(i) - mx)^2} \sqrt{\sum_i (y(i - d) - my)^2}}$$

The above equation involves convolving the sum of Signal X with Signal Y and normalizing based on the product of the magnitude of the two signals. The result of the equation is a score for each point in a time series. The value of the score indicates how well the two signals align in phase and magnitude. The maximum score is achieved when the two curves are identical and aligned in terms of time offset. For the normalized formula above, the max score is 1 and the min score is 0.

The template would be a predefined signal (Signal X) which represents an event which was previously characterized like someone bumping the OR table. A window of data from the sensors is acquired over a length of time and is longer than the template period. The acquired data is Signal Y. The cross-correlation algorithm may determine the time when a bump occurred, as well as a score indicating how well it matches the provided template. In this case, the threshold would be the score. Once the score is determined to be over the threshold of confidence there was a table bump, the algorithm could then figure out at what time the table bump occurred.

Thus, cross correlation may be understood as a way to compare two signals over time, rather than just comparing the signal to some threshold at an instant in time. In accordance with one or more embodiments, the cross-correlation algorithm is applied as a way of checking a strain profile generated based on signals from the sensors and comparing the strain profile to a signature for a particular type of vibration, which may occur, for example, as a result of knocking into the cart, dropping an instrument on the cart, etc.

At 1155, once it is determined in operation 1140 that the robot arm is to be repositioned, a new reference state is captured at the new position and the processor begins to once again compare strain signatures/profiles to detect or predict an anomalous condition. As previously indicated, repositioning of the robot arm may occur, for example, when a current phase of the amputation has been completed and a new phase of the operation is to be performed at a different location. During the repositioning process, the processor 10 may continue to monitor loading on the arm to ensure that no unexpected loading conditions exist.

At 1160, once the robot arm and saw have been disabled, the surgeon or a technician may take action to correct the one or more factors that were responsible for causing the strain profile change. This may involve, for example, merely waiting until vibrations caused by an inadvertent bump stop. In another case, this may involve repositioning the robot arm and bone saw. In yet another case, the corrective action may involve replacing the saw (if damaged), repairing or replacing the holding arm when it breaks (e.g., the mechanical structure that holds the robot), or waiting for a period of time until the patient has calmed down or is in a more stable state. In another case, the technician may change the mechanical loading on the robot arm, for example, by repositioning the arm, augmenting physical interaction with the arm or too, and/or removing components.

Detection Examples

The following examples describe practical situations where anomalies or other conditions relating to the operation of the robot arm and/or the medical tool may be expected to occur. For each situation, the memory 20 of the system may store a corresponding detection algorithm (or model) that may be used as a basis for analyzing the strain profiles generated from the sensors arranged on the robot arm. Each algorithm (or model) may use different maximum limits and margins and/or may perform different forms of analysis, for example, based on the specific anomaly or condition that algorithm is intended to preemptively detect.

FIGS. 6A to 6C illustrate an example of when an excessive load is detected on the robot arm 50. The excessive load may be caused, for example, as a result of too much downward force being applied to the bone saw in the case where the robot arm 50 is in a locked state. The force may be applied, for example, based on control from the robot and/or based on force applied by a user on the bone saw. As illustrated in FIG. 6A, strain gauges S1 and S3 detect the excessive load in the form of a bending moment that exceeds a predetermined threshold or critical value. The direction of sensitivity of the strain gauges S1 and S3 (and also S2 and S4) may be substantially aligned with the longitudinal axis of the horizontal linkage member of the holding arm to which they are mounted. This orientation makes strain gauges S1 to S4 sensitive to detecting bending forces in a plane normal to the floor and linear in nature. The bending forces may include moments about an axis perpendicular to the longitudinal cross bar of the horizontal linkage and parallel to the floor.

FIG. 6B illustrates a cross-sectional view of the robot arm 50 at the location of the strain gauges. In this example, the bending moment imposes a tensile force F1 on strain gauge S1 and a compression force F2 on strain gauge S3. The strain gauges S1 and S3 generate signals indicative of these forces. The signals are then processed by processor 10 to generate a changing strain profile (in operation 1135) that exceeds a critical value (in operation 1145).

In one embodiment, the critical value may be less than the level of strain required to produce an anomalous condition. For example, the critical value may be just below (e.g., by a predetermined margin) a strain level that would interfere with control of the saw. In another example, the critical value may be based on a predetermined amount of vibration (e.g., of the holding arm and/or surgical table) determined, for example, through signature matching. When the processor 10 generates a strain profile (from the signals from strain gauges S1 and S3) that equals or exceeds the critical value, preemptive action may be taken to prevent the anomalous condition from occurring, which, for example, may include disabling the robot arm and bone saw as previously discussed with respect to operation 1150 in the method of FIG. 3.

FIG. 6C is a graph illustrating examples of strain profiles generated by processor 10 based on the signals received from strain gauges S1 to S4. In the graph, the top limit 1410 corresponds to a predetermined maximum positive (tensile) strain and the lower limit 1420 corresponds to a predetermined negative (compressive) strain. These limit values correspond to unsafe limits that, for example, may produce a malfunction in the robot arm that poses a threat to the patient or which may otherwise be considered unacceptable or unsafe.

The strain profiles include strain profile 1430 generated based on signals output from strain gauge S1, strain profile 1440 generated based on signals output from strain gauge S2, strain profile 1450 generated based on signals output from strain gauge S3, and strain profile 1460 generated based on signals output from strain gauge S4. Because the bending moment on the robot arm 50 mainly affects strain gauges S1 and S3, the strain profiles 1440 and 1460 corresponding to strain gauges S2 and S4 are very low, e.g., do not approach any of the positive or negative maximum limits 1410 and 1420 throughout the duration of the graph. Conversely, the strain profiles 1430 and 1450 produce very prominent peak load signals (see circles) that come within predetermined margins 1480 and 1490 of the positive and negative maximum limits, respectively. The predetermined margins may be, for example, 25% from the positive or negative maximum limits.

In one embodiment, current values from one or more of the strain gauges may be compared to one or more corresponding prior values from the strain gauges to determine a malfunction or condition of the robot arm or tool or some other condition during the operation. In FIG. 6C, this is illustrated by the values generated by strain gauge S1 at points P1 and P2. In this embodiment, processor 10 may continuously compare current values of the one or more strain gauges to prior values and if the difference between them is equal to or greater than a predetermined difference value $\Delta$, then the processor may determine, for example, that there is a high probability that a malfunction may occur or is occurring in the robot arm or otherwise that it is unsafe to continue the operation.

Figure 7:
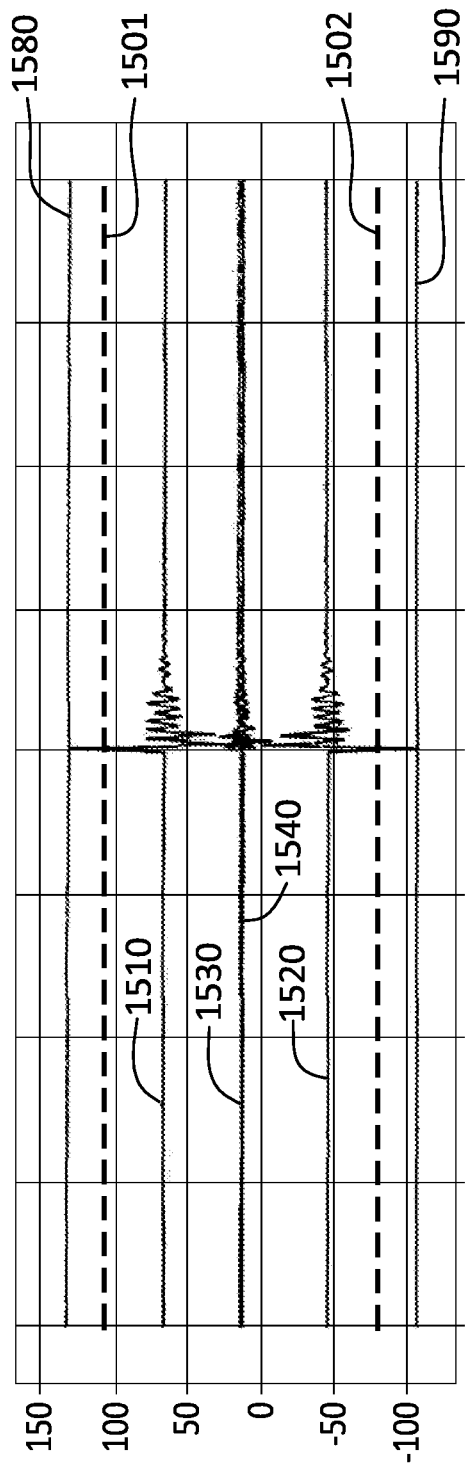
FIG. 7 illustrates detection of a state of a robot arm according to another embodiment.

FIG. 7 is a graph illustrating an example of when impulse forces (of a short duration) impinge on the robot arm. Such impulses may exceed or distort the imaging capabilities of the robot vision system. Examples of impulse forces that may cause these effects include bumps applied to the robot arm or surgical table. When this occurs, high frequency variations may be produced that are short enough in duration that do not immediately trip safety interlocks on the robot arm. In FIG. 7, the impulse forces in this example are most prominently evident in the strain profile 1510 corresponding to strain gauge S1 and the strain profile 1520 corresponding to strain gauge S3. The impulse forces show up in a much lesser extend in the strain profiles 1530 and 1540 of strain gauges S2 and S4, respectively. Because the impulse forces in the strain profiles of strain gauges S1 and S3 cause the signature to deviate significantly (as a result of performing signature matching), an anomalous condition may be detected that may cause the processor 10 to suspend operation of the robot arm and bone saw for at least a predetermined time, as indicated in operation 1150 of FIG. 3. In one embodiment, the impulse forces in the strain profiles of strain gauges S1 and S3 exceed predetermined margins 1501 and 1502 relative to positive and negative maximum strain limits 1580 and 1590 (see circled portions). In this example, the predetermined margins may be set to be 30% from their respective maximum limits (as indicated by the dotted lines).

Generating the strain profiles in the manner indicated in FIG. 7 may also allow for detection of vibrations, which may produce robot arm excursions at rates which exceed the imaging capabilities of the robot vision system. In one embodiment, a hardware implementation may be used to generate and detect excessive values of the strain profiles of FIG. 7. Such a hardware implementation may mitigate risks associated with software failures that may result from image-based detection.

Figure 8:
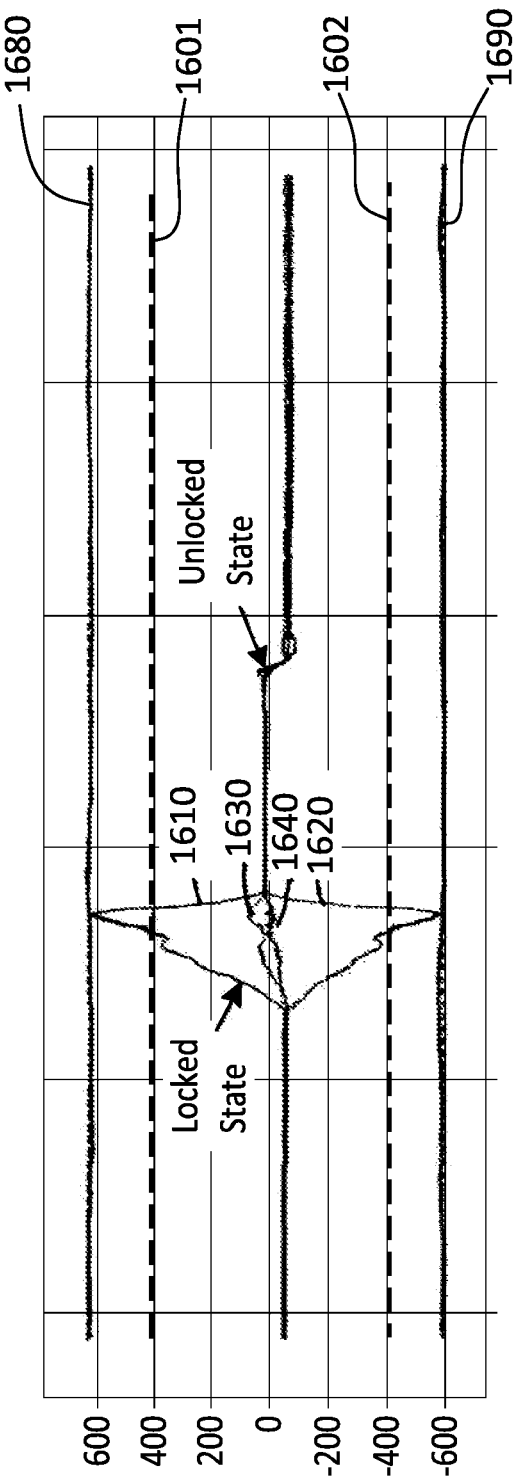
FIG. 8 illustrates detection of a state of a robot arm according to another embodiment.

FIG. 8 is a graph illustrating an example of detecting when the horizontal linkage of the robot arm is in a locked or unlocked state. In this graph, predetermined positive and negative maximum strain limits 1680 and 1690 are set and strain profiles generated by processor 10 for all four strain gauges S1 to S4 are included. The strain profiles 1610 and 1620 of strain gauges S1 and S3 exceed respective margins 1601 and 1602, indicating that the robot arm has entered a locked state, e.g., locking the robot arm may generate a recognizable and detectable strain profile that is substantially triangular in form as shown in FIG. 8. In one embodiment, the magnitude of the strain profiles 1610 and 1620 may indicate the strength of locking.

The strain profiles 1630 and 1640 of strain gauges S2 and S4 demonstrate much less response to the locking condition. At a later point in time, a smaller but detectable decrease in the strain profiles for all four stain gauges present a signature that identifies when the robot arm has been unlocked. The algorithm used to detect these states may also be capable of detecting wear of the robot arm and/or medical tool over time. The difference between steady state high and low strain may eventually increase over time as parts wear. The present algorithm may therefore be used to predict failure or the need for preventive maintenance before the failure actually occurs.

Figure 9:
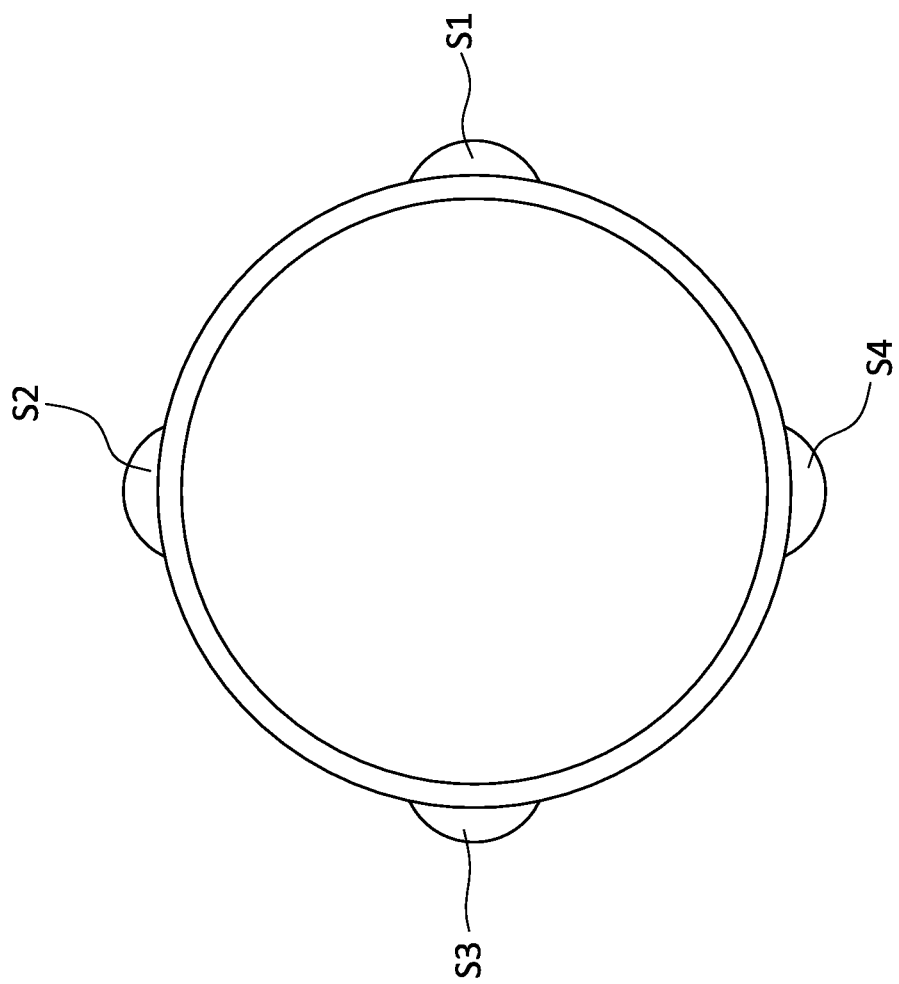
FIG. 9 illustrates another example of an arrangement of sensors on a robot arm.

FIG. 9 illustrates an arrangement of strain gauges on the robot arm according to another embodiment. In this embodiment, all four strain gauges are arranged symmetrically at a predetermined location of the robot arm 50. For example, the strain gauges may be arranged at radially symmetrically relative to a cross-section of the robot arm, e.g., at locations 0°, 90°, 180°, and 270° positions.

Figure 10:
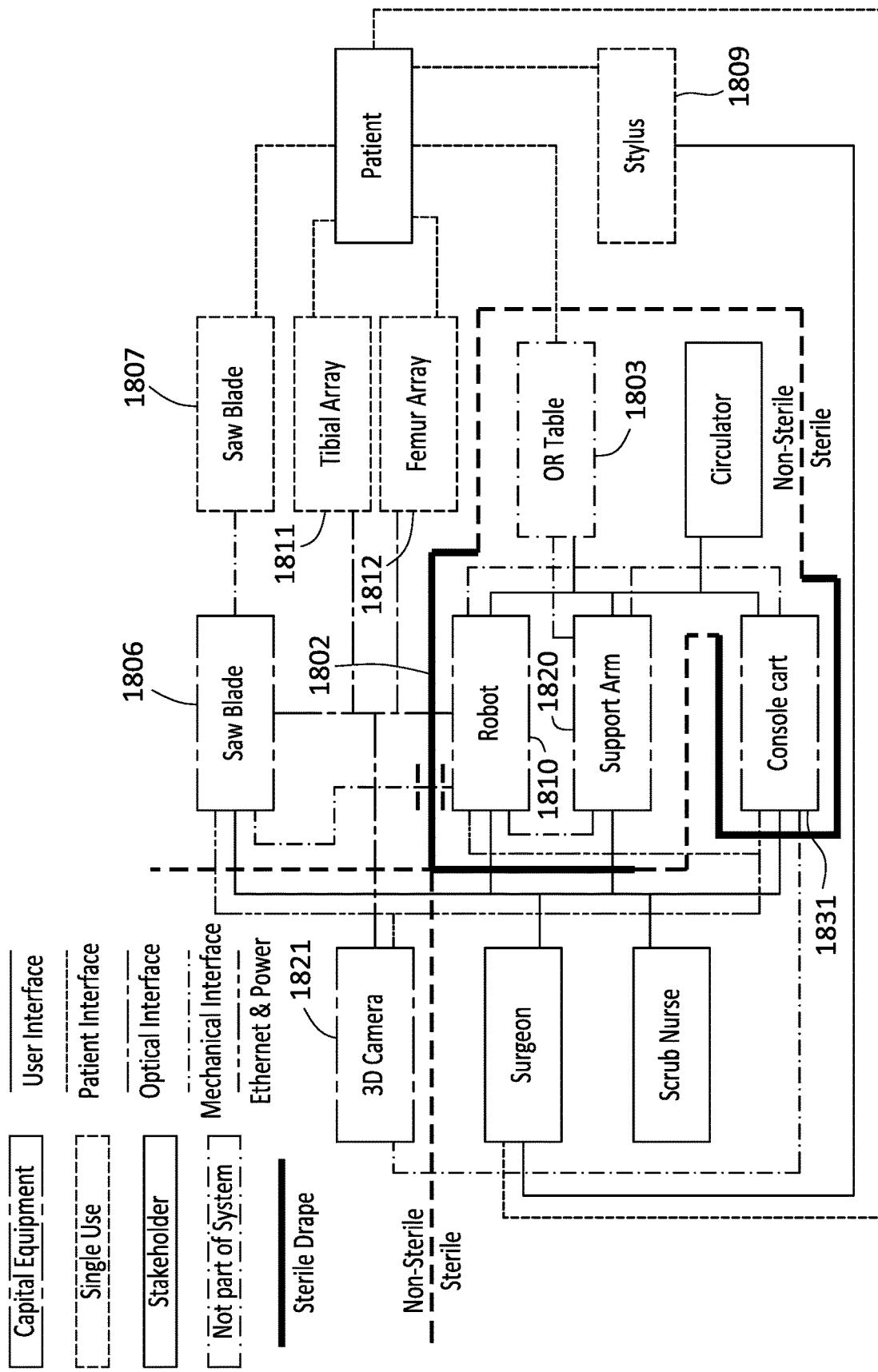
FIG. 10 illustrates an example of how a robot and robot arm may be used to perform an operation.

FIG. 10 illustrates an example of how the robot and robot arm may be used to perform an operation in a practical scenario. In this example, it is assumed that the robot arm is holding a bone saw, but the arm may hold a different type of tool in another embodiment.

Referring to FIG. 10, the robot 1810 and its attendant robot arm 1820 may be located in an operating room 1801 including a sterile drape 1802. The operating room includes an operating table 1803 supporting a patient (as labeled) having a limb to be amputated, in this example, using the bone saw. The bone saw includes a bone saw controller 1806 for controlling a saw blade 1807 held by the robot arm. The bone saw is to amputate at a vicinity of a tibial array 1811 and femur array 1812 including infrared or other sensors to facilitate image capture by a three-dimensional camera 1821, as previously described. The surgeon and a nurse (as labeled) are also in the room for guiding the operation using the robot and for assisting in various stages of the operation. A circulator and stylus 1809 may be used along with a cart 1831 for operating and transporting the robot.

In accordance with one or more of the aforementioned embodiments, a system and method are provided to control a robot arm to perform a predetermined function. In one example, the robot arm may hold a medical tool for performing a medical procedure on a patient. The medical procedure may be performed for a surgical, diagnostic, exploratory, or another purpose depending, for example, on the type of tool held by the robot arm. The arm may include one or more sensors to guide a processor (inside or separate from the robot) for controlling the arm.

In one or more embodiments, algorithms stored in a memory may control a processor to detect a state of operation of the robot arm based on one or more of the sensor signals. The state of operation is recognized by the algorithm(s) to determine a probability of whether a condition will occur or is occurring, which condition may be indicative of a malfunction or other condition of the robot or robot arm or which might otherwise pose a threat to patient safety. The probability may be defined, for example, within a predetermined marginal range of an upper and/or lower limit corresponding to the condition. For example, the marginal range may be within 30% of the upper or lower limit. When such a probability is determined to exist, a processor generates signals for quickly disabling the robot arm at least temporarily (e.g., with a response time in the range of milliseconds) to prevent the condition from occurring or continuing to occur or to take other precautionary action(s). Examples of factors that may cause the condition to occur include vibrations, bumping, the application of unexpected, sudden (impulsive) or excessive forces on the arm, and various defects and conditions associated with locked and unlocked states of the arm. All of these control features may be implemented to ensure the best possible safety of the patient, while at the same time realizing the increase accuracy and other benefits of using a robot to perform medical procedures.

The methods, processes, and/or operations described herein may be performed by code or instructions to be executed by a computer, processor, controller, or other signal processing device. The code or instructions may be stored in the non-transitory computer-readable medium as previously described in accordance with one or more embodiments. Because the algorithms that form the basis of the methods (or operations of the computer, processor, controller, or other signal processing device) are described in detail, the code or instructions for implementing the operations of the method embodiments may transform the computer, processor, controller, or other signal processing device into a special-purpose processor for performing the methods herein.

The processors, controllers, sensors, and other signal generating and signal processing features of the embodiments disclosed herein may be implemented in logic which, for example, may include hardware, software, or both. When implemented at least partially in hardware, the processors, controllers, sensors, and other signal generating and signal processing features of the embodiments may be, for example, any one of a variety of integrated circuits including but not limited to an application-specific integrated circuit, a field-programmable gate array, a combination of logic gates, a system-on-chip, a microprocessor, or another type of processing or control circuit.

When implemented in at least partially in software, the processors, controllers, sensors, and other signal generating and signal processing features of the embodiments may include, for example, a memory or other storage device for storing code or instructions to be executed, for example, by a computer, processor, microprocessor, controller, or other signal processing device. The computer, processor, microprocessor, controller, or other signal processing device may be those described herein or one in addition to the elements described herein. Because the algorithms that form the basis of the methods (or operations of the computer, processor, microprocessor, controller, or other signal processing device) are described in detail, the code or instructions for implementing the operations of the method embodiments may transform the computer, processor, controller, or other signal processing device into a special-purpose processor for performing the methods described herein.

Although the various example embodiments have been described in detail with particular reference to certain exemplary aspects thereof, it should be understood that the invention is capable of other example embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

I claim:

1. A method for managing a surgical robot having an arm configured to hold a medical tool, comprising:
   receiving a set of sensor signals from sensors on the arm;
   generating a time domain profile based on the set of sensor signals, wherein the time domain profile includes a plurality of points spanning a specified timeframe;
   comparing the time domain profile to at least one time domain signature, wherein the time domain signature includes a plurality of points spanning the specified timeframe;
   determining a state of the arm based on results of the comparison; and
   changing operation of the robot based on the state of the arm, wherein the state of the arm is indicative of a predetermined condition that has occurred or will likely occur eminently and wherein changing operation of the arm prevents the condition from occurring or continuing.

2. The method of claim 1, wherein the set of sensor signals includes one or more strain signals.

3. The method of claim 1, wherein the set of sensor signals includes one or more accelerometer signals, gyro signals, potentiometer signals, or Linear Variable Differential Transformer and Transducer (LVDT) signals.

4. The method of claim 1, wherein the at least one time domain signature includes a vibration profile.

5. The method of claim 1, wherein changing operation of the arm is performed when the time domain profile matches the at least one time domain signature by a predetermined percentage.

6. The method of claim 1, wherein:
   the at least one time domain signature includes at least one margin value;
   the state of the arm corresponds to at least one of the set of sensor signals having a value in a predetermined range that is less than a sensor value corresponding to condition; and
   the margin value corresponds to a lower value of the predetermined range.

7. The method of claim 6, wherein:
   the at least one time domain signature includes a value of a first strain signal at a first time;
   comparing the time domain profile to the at least one time-based signature includes comparing a value of the first strain signal at a second time to the value of the first strain signal at the first time; and
   determining the state of the arm includes determining that a difference between the value of the first strain signal at the first time and the value of the first strain signal at the second time is greater than a predetermined difference value.

8. The method of claim 1, wherein changing operation of the arm includes disabling operation of the arm for at least a temporary period of time.

9. The method of claim 1, wherein the condition corresponds to a force on the arm that causes the arm to deviate in an unintended direction.

10. The method of claim 9, wherein the condition corresponds to a force on the arm caused by a bump or vibration.

11. The method of claim 1, wherein the condition corresponds to improper or unsafe locking state of the robot arm during an operation.

12. A system for managing a surgical robot having an arm configured to hold a medical tool, comprising:
   a memory configured to store one or more algorithms; and
   a processor configured to
      receive a set of sensor signals; and
      execute the one or more algorithms to control the arm that includes sensors that generate the set of sensor signals, wherein the time domain profile includes a plurality of point spanning a specified timeframe, the one or more algorithms to generate a time-based profile from the set of sensor signals, compare the time domain profile to at least one time domain signature, wherein the time domain signature includes a plurality of points spanning the specified timeframe, determine a state of the arm based on results of the comparison, and generate signals to change operation of the robot based on the state of the robot arm, wherein the state of the arm is indicative of a predetermined condition that has occurred or will likely occur eminently and wherein changing operation of the arm prevents the condition from occurring or continuing.

13. The system of claim 12, wherein the set of sensor signals includes a set of strain signals.

14. The system of claim 12, wherein the set of sensor signals includes one or more accelerometer signals, gyro signals, potentiometer signals, or Linear Variable Differential Transformer and Transducer (LVDT) signals.

15. The system of claim 12, wherein the at least one time domain signature includes a vibration profile.

16. The system of claim 12, wherein changing operation of the arm is performed when the time domain profile matches the at least one time domain signature by a predetermined percentage.

17. The system of claim 12, wherein:
   the at least one time domain signature corresponds to at least one margin value;
   the state of the arm corresponds to at least one of the set of sensor signals having a value in a predetermined range that is less than a sensor value corresponding to the condition; and
   the margin value corresponds to a lower value of the predetermined range.

18. The system of claim 12, wherein:
   the at least one time domain signature includes a value of a first strain signal at a first time; and
   the one or more algorithms are to cause the processor to compare a value of the first strain signal at a second time to the value of the first strain signal at the first time and determine that a difference between the value of the first strain signal at the first time and the value of the first strain signal at the second time is greater than a predetermined difference value.

19. The system of claim 12, wherein the one or more algorithms are to cause the processor to disable operation of the robot arm for at least a temporary period of time.

20. The system of claim 12, wherein the condition corresponds to a force on the arm that causes the arm to deviate in an unintended direction.

* * * * *